United States Patent [19]

Vogt

[11] 4,002,639

[45] Jan. 11, 1977

[54] 2-(SUBSTITUTED PHENYL)-DIBENZ[b,f][1,2,4]TRIAZOLO-[4,3-d][1,4]OXAZEPIN OR THIAZEPIN-3(2H)-ONES

[75] Inventor: Berthold Richard Vogt, Yardley, Pa.

[73] Assignee: E. R. Squibb & Sons, Inc., Princeton, N.J.

[22] Filed: Mar. 31, 1975

[21] Appl. No.: 563,769

[52] U.S. Cl. .................. 260/308 C; 260/327 B; 260/239.3 T; 260/333; 424/269

[51] Int. Cl.$^2$ ............. C07D 498/04; C07D 513/14

[58] Field of Search .................. 260/308 C

[56] References Cited

UNITED STATES PATENTS

| | | | |
|---|---|---|---|
| 3,853,881 | 12/1974 | Szmuszkovicz | 260/308 C |
| 3,853,882 | 12/1974 | Szmuszkovicz | 260/308 C |
| 3,853,904 | 12/1974 | Szmuszkovicz | 260/308 C |
| 3,862,950 | 1/1975 | Szmuszkovicz | 260/308 C |

*Primary Examiner*—Alton D. Rollins
*Attorney, Agent, or Firm*—Lawrence S. Levinson; Merle J. Smith; Stephen B. Davis

[57] ABSTRACT

Compounds of the following formula

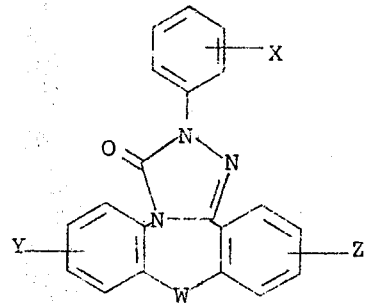

wherein W is O or S; and X, Y and Z are independently selected from hydrogen, fluorine, bromine, chlorine, trifluoromethyl, lower alkyl and lower alkoxy; are disclosed. These compounds are useful as antiinflammatory agents.

6 Claims, No Drawings

2-(SUBSTITUTED PHENYL)-DIBENZ[b,f][1,2,4]TRIAZOLO-[4,3-d][1,4]OXAZEPIN OR THIAZEPIN-3(2H)-ONES

BACKGROUND OF THE INVENTION

Various dibenzo[b,f][1,2,4]triazolo[4,3-d][1,4]-oxazepin and thiazepin-3(2H)-ones as well as such compounds substituted in the 2-position by an alkyl, alkylamino, alkylaminoalkyl, pyrrolidino, piperidino or N-methyl piperazino group are taught to possess useful tranquilizing and antidepressant activity in U.S. Pat. Nos. 3,853,881 and 3,853,904 to Szmuszkovicz.

SUMMARY OF THE INVENTION

This invention relates to new dibenzo[b,f][1,2,4]-triazolo[4,3-d][1,4]oxazepin and thiazepin-3(2H)-ones substituted in the 2-position by a phenyl or substituted phenyl group of the formula

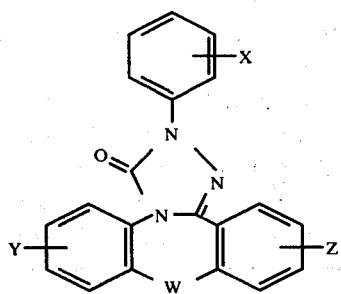

The symbols have the following meaning in formula I and throughout this specification W is O or S.

X, Y, and Z are independently selected from hydrogen, fluorine, bromine, chlorine, trifluoromethyl, lower alkyl, and lower alkoxy.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 3 carbons, i.e. methyl, ethyl, n-propyl, i-propyl. The lower alkoxy groups include such lower alkyl groups attached to an oxygen, i.e. methoxy, ethoxy, n-propoxy, i-propoxy.

Preferred are the compounds wherein X, Y, and Z are hydrogen and most preferred is the compound wherein W is O.

The new compounds of this invention are prepared by reacting a compound of the formula

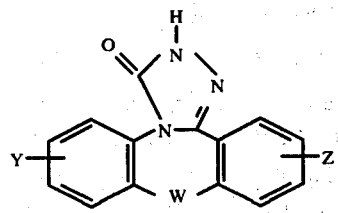

with at least from about 0.5 to a large excess, preferably at least from about 0.8 to about 100, molar equivalents of a substituted phenyl-halide of the formula

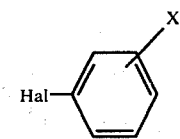

wherein Hal is either bromine or chlorine and X is as defined above. The reaction is performed in the presence of a copper catalyst and a solvent containing from about 0.5 to about 1000, preferably from about 0.8 to about 100, molar equivalents of an appropriate hydrogen halide acceptor. The phenyl-halide of formula III can also serve as the solvent or solvents such as N,N-dialkylformamides and N,N-dialkyl alkanoyl amides wherein the alkyl and alkanoyl radicals have 1–4 carbons such as N,N-dimethylformamide, N,N-dimethylacetamide and the like; dialkyl sulfoxides of 2–6 carbons such as dimethyl sulfoxide and the like; and alkylphosphorous triamides of 4–10 carbons such as hexamethylphosphorous triamide can be employed. The preferred copper catalysts are powdered copper metal, copper oxides, cuprous and cupric salts. Acceptable hydrogen halide acceptors include alkali metal (preferably sodium or potassium) carbonates, bicarbonates, or lower alkyl carboxylic acid salts thereof (e.g., acetates). The reaction is carried out at from about 50° C to about 200° C, preferably at from about 90° C to about 180° C, for from about ¼ to about 72 hours, preferably for from about ½ to about 14 hours. The product is isolated in a conventional manner. For example, the reaction mixture is diluted with methylene chloride, washed with dilute aqueous ammonium hydroxide and chromatographed. (See Vogt, U.S. Pat. Application Ser. No. 404,071 and Belgium Pat. No. 748,555.)

Alternatively, the final product of formula I can be prepared by adding the compound of formula II in dry dimethylformamide to a stirred suspension of a 57% mineral oil dispersion of sodium hydride in dry dimethylformamide at a rate so as to maintain the temperature of the reaction mixture at from about 30° to about 40° C. The mixture is heated until the evolution of hydrogen ceases and the reactant of formula is added.

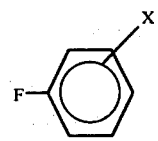

This reaction mixture is heated at from about 30° to about 75° C for from about 1 hour to about 24 hours, preferably 3 hours at 60°–70° C followed by 12 hours at 35° C (Boswell et al., Jour. of Med. Chem., 1974, Vol. 17, No. 9, p. 1000–1008). The product is isolated in a conventional manner. For example, the reaction mixture is diluted with methylene chloride, washed with dilute aqueous ammonium hydroxide and chromatographed.

The compounds of formula II can be prepared according to the methods set forth in U.S. Pat. Nos. 3,853,881 and 3,853,904. Alternatively, these compounds can also be prepared by reacting compounds of the formula

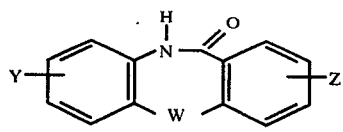

with phosphorous oxychloride to form the intermediates

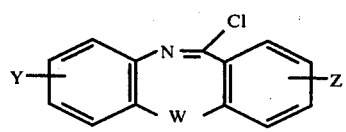

which are then reacted at reflux temperature with ethyl carbazate in dry DMF, preferably under argon, to yield the compounds of formula II.

The compounds of formula I are useful in treating inflammation in mammalian species, e.g., rats, dogs, cats, monkeys, etc. Joint tenderness and stiffness (in conditions such as rheumatoid arthritis) are relieved by the above described compounds.

The compounds of this invention are formulated for use as anti-inflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts of 100 mg/70kg/day to 2 g/70kg/day, preferably 100 mg/70kg/day to 1 g/70kg/day.

The following examples are specific embodiments of this invention. All temperatures are expressed in degrees Centigrade.

EXAMPLE 1

2-Phenyldibenzo[b,f][1,2,4]triazolo[4,3-d][1,4]oxazepin3(2H)-one a. 11-Chlorodibenz[b,f][1,4]oxazepine 23.4 g. (0.1 mole) of 10,11-dihydrodibenz[b,f][1,4]-oxazepin-11-one and 7.5 ml. of dimethylaniline in 200 ml. of phosphorous oxychloride are refluxed with stirring for 5 hours under a drying tube. The reaction is stripped. The residue is azeotroped with benzene and partitioned between ice water and ether. The aqueous phase is washed with ether and the ether phases are combined, washed with cold dilute hydrochloric acid, dried and stripped to give 25.6 g. of crude 11-chlorodibenz[b,f][1,4]oxazepine as an oil which solidifies on standing at 5°; m.p. 53°–55°.

b. Dibenzo[b,f][1,2,4]triazolo[4,3-d][1,4]oxazepin-3(2H)-one 14.59 g. of 11-chlorodibenz[b,f][1,4]oxazepine and 13.25 g. of ethyl carbazate in 75 ml. of dry DMF are refluxed for 18 hours under argon. The reaction is cooled in an ice bath and the product is filtered off, washed with acetone and then ether to give 5.6 g. of dibenzo[b,f][1,2,4]triazolo[4,3-d][1,4]oxazepin-3(2H)-one; m.p. 261°–262°.

c. 2-Phenyldibenzo[b,f][1,2,4]triazolo[4,3-d][1,4]oxazepin-3(2H)-one 2.5 g. (0.01 mole) of dibenzo[b,f][1,2,4]triazolo[4,3-d][1,4]oxazepin-3(2H)-one, 2.5 g. of copper powder and 1.75 g. of potassium acetate are refluxed in 50 ml. of bromobenzene for 6 hours. The reaction mixture is cooled, diluted with 50 ml. of methylene chloride, some Celite is stirred into the mixture, and the entire mixture is then filtered through a Celite pad. The Celite pad is washed with 50 ml. of methylene chloride. The filtrates are combined and washed with 100 ml. of 1N $NH_4OH$. The aqueous phase is back-extracted with more methylene chloride and the organic extracts are combined, dried over anhydrous sodium sulfate, filtered and stripped to dryness to yield 3.3 g. of an off-white solid material. This material is chromatographed on a silica gel column (1⅛ inches × 9 inches). The column is eluted with 150 ml. of methylene chloride, 400 ml. of $CH_2Cl_2$:EtOAc (8:2), 400 ml. of $CH_2Cl_2$:EtOAc (1:1), and 300 ml. of ethyl acetate. The first 300 ml. of eluate yields 2.5 g. of 2-phenyldibenzo[b,f][1,2,4]triazolo[4,3-d]-[1,4]oxazepin-3(2H)-one; m.p. 176°–177°.

EXAMPLE 2

2-Phenyldibenzo[b,f][1,2,4]triazolo[4,3-d][1,4]thiazepin-3(2H)-one

Following the procedure of example 1c but substituting an equimolar amount of dibenzo[b,f][1,2,4]-triazolo[4,3-d]-[1,4]thiazepin-3(2H)-one for the dibenzo[b,f][1,2,4]triazolo[4,3-d][1,4]oxazepin-3(2H)-one, one obtains 2-phenyldibenzo[b,f][1,2,4]-triazolo[4,3-d]triazepin-3(2H)-one.

EXAMPLES 3–33

Following the procedure of either example 1c or 2 but employing the substituted dibenzo[b,f][1,2,4]-triazolo[4,3-d][1,4]oxazepin or thiazepin-3(2H)-one shown below in Col. I the product shown in Col. II is obtained.

| | Col. I | | | | Col. II | | | |
|---|---|---|---|---|---|---|---|---|
| Ex. No. | W 9 | Y {5 | 6 | 7 | 8} | Z {10 | 11 | 12 | 13} |

| Ex. No. | W 9 | 5 | 6 | 7 | 8 | 10 | 11 | 12 | 13 |
|---|---|---|---|---|---|---|---|---|---|
| 3 | O | H | H | Cl | H | H | H | H | H |
| 4 | S | H | H | Cl | H | H | H | H | H |
| 5 | O | H | H | F | H | H | H | H | H |
| 6 | S | H | H | H | H | H | F | H | H |
| 7 | O | Cl | H | H | H | H | H | H | H |
| 8 | S | H | H | H | Cl | H | H | H | H |
| 9 | O | H | Br | H | H | H | H | H | H |
| 10 | O | H | H | Cl | H | H | Cl | H | H |
| 11 | S | H | H | Cl | H | H | Cl | H | H |
| 12 | O | H | F | H | H | H | F | H | H |
| 13 | S | H | H | Br | H | Br | H | H | H |
| 14 | O | CH₃ | H | H | H | H | H | H | H |
| 15 | S | H | H | CH₃ | H | H | H | H | H |
| 16 | O | H | H | H | C₂H₅ | H | H | H | H |
| 17 | S | H | H | H | H | H | C₂H₅ | H | H |
| 18 | O | H | H | H | H | n-C₃H₇ | H | H | H |
| 19 | O | H | CH₃ | H | H | H | CH₃ | H | H |
| 20 | S | H | H | H | CH₃ | CH₃ | H | H | H |
| 21 | O | H | H | Cl | H | H | C₂H₅ | H | H |
| 22 | O | H | H | OCH₃ | H | H | H | H | H |
| 23 | S | H | H | H | H | H | OC₂H₅ | H | H |
| 24 | O | H | H | OCH₃ | H | H | OCH₃ | H | H |
| 25 | O | OCH₃ | H | H | H | H | H | CH₃ | H |
| 26 | S | H | OCH₃ | H | H | H | Cl | H | H |
| 27 | O | H | H | OCH₃ | H | H | H | F | H |
| 28 | O | H | H | H | H | H | H | i-OC₃H₇ | H |
| 29 | O | H | CF₃ | H | H | H | H | H | H |
| 30 | S | H | H | H | H | H | H | H | CF₃ |
| 31 | O | H | H | CF₃ | H | H | Cl | H | H |
| 32 | O | H | H | H | H | H | H | Cl | H |
| 33 | S | H | H | H | H | H | H | Br | H |

EXAMPLES 34–39

Following the procedure of Example 1c but substituting for the bromobenzene the reactants listed below in Col. I one obtains the final products listed below in Col. II.

| Ex. | Col. I | Col. II |
|---|---|---|
| 34 | 1,3-dibromobenzene | 2-(3-bromophenyl)dibenzo[b,f]-[1,2,4]triazolo[4,3-d] [1,4]-oxazepin-3(2H)-one. |
| 35 | 1,4-dichlorobenzene | 2-(4-chlorophenyl)dibenzo[b,f]-[1,2,4]triazolo[4,3-d] [1,4]-oxazepin-3(2H)-one. |
| 36 | 2-methyl-bromobenzene | 2-(2-methylphenyl)dibenzo[b,f]-[1,2,4]triazolo[4,3-d] [1,4]-oxazepin-3(2H)-one. |
| 37 | 4-ethoxy-bromobenzene | 2-(4-ethoxyphenyl)dibenzo[b,f]-[1,2,4]triazolo[4,3-d] [1,4]-oxazepin-3(2H)-one. |
| 38 | 3-propyl-bromobenzene | 2-(3-propylphenyl)dibenzo[b,f]-[1,2,4]triazolo[4,3-d] [1,4]-oxazepin-3(2H)-one. |
| 39 | 4-trifluoromethyl-bromobenzene | 2-[4-(trifluoromethyl)phenyl]-dibenzo[b,f] [1,2,4]triazolo[4,3-d]-[1,4]-oxazepin-3 (2H)-one. |

Similarly, by employing the substituted phenylhalides of examples 34 to 39 in the procedures of examples 2 to 33, other compounds within the scope of the invention are obtained.

EXAMPLE 40

2-(3-Chlorophenyl)dibenzo[b,f][1,2,4]triazolo[4,3-d][1,4]-oxazepin-3(2H)-one

To a stirred suspension of 1.12 g. (0.025 mole) of a 57% mineral oil dispersion of sodium hydride in 20 ml. of dry dimethylformamide is added a solution of 4.25 g. (0.017 mole) of dibenzo[b,f][1,2,4]triazolo[4,3-d][1,4]-oxazepin-3(2H)-one in 10 ml. of dry dimethylformamide at a rate so as to maintain the temperature of the reaction mixture at Ca. 32°–35° and to maintain a steady evolution of $H_2$. After the addition is complete, the mixture is heated to about 50° until the evolution of hydrogen ceases. 2.76 g. (0.021 mole) of 3-fluorochlorobenzene is added to the reaction mixture at a rate so as to maintain a temperature of 50°–60°. After the addition is complete, the reaction mixture is stirred at 60°–70° for 3 hours and then at 35° for an additional 12 hours. The reaction mixture is cooled, diluted with a large excess of water and extracted with methylene chloride. The solvent is evaporated to give the crude title compound which is purified by chromatography as described in Example 1c.

EXAMPLES 41–44

Following the procedure of example 40 but substituting for the 3-fluoro-chlorobenzene the fluorobenzenes listed below in Col. I, one obtains the final products listed below in Col. II.

| Ex. | Col. I | Col. II |
|---|---|---|
| 41 | fluorobenzene | 2-Phenyldibenzo[b,f] [1,2,4]-triazolo[4,3-d] [1,4]oxazepin-3(2H)-one. |
| 42 | 4-fluoro-bromobenzene | 2-(4-bromophenyl)dibenzo[b,f]-[1,2,4]triazolo[4,3-d] [1,4]-oxazepin-3(2H)-one. |
| 43 | 3-trifluoromethyl-fluorobenzene | 2-[3-(trifluoromethyl)phenyl]-dibenzo[b,f] [1,2,4]triazolo-[4,3-d][1,4]oxazepin-3(2H)-one. |
| 44 | 2-methoxy-fluorobenzene | 2-(2-methoxyphenyl)dibenzo[b,f]-[1,2,4]triazolo[4,3-d] 1,4]-oxazepin-3(2H)-one. |

Similarly, by employing any of the various substituted dibenzo[b,f][1,2,4]triazolo[4,3-d]oxazepin or thiazepin3(2H)-ones of examples 2 to 33 in the procedure of examples 40 to 44, other compounds within the scope of the invention are obtained.

What is claimed is:
1. A compound of the formula:

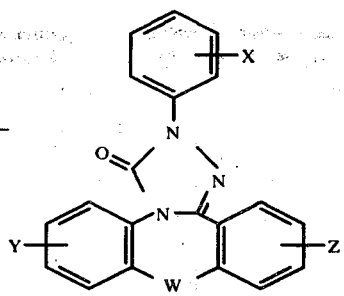

wherein W is O or S; and X, Y and Z are independently selected from the group consisting of hydrogen, bromine, chlorine, fluorine, lower alkyl of 1 to 3 carbon atoms, lower alkoxy of 1 to 3 carbon atoms, and trifluoromethyl.

2. The compound of claim 1 wherein Y and Z are hydrogen.
3. The compound of claim 2 wherein W is O.
4. The compound of claim 3 wherein X is hydrogen.
5. The compound of claim 2 wherein W is S.
6. The compound of claim 5 wherein X is hydrogen.

* * * * *

UNITED STATES PATENT AND TRADEMARK OFFICE
CERTIFICATE OF CORRECTION

PATENT NO. : 4,002,639
DATED : January 11, 1977
INVENTOR(S) : Vogt

It is certified that error appears in the above-identified patent and that said Letters Patent are hereby corrected as shown below:

Col. 2, line 49, "the reactant of formula is added." should read --the reactant of formula IV is added.--

Col. 4, line 46, "[4,3-d]-[1,4]" should read --[4,3-d][1,4]--.

Col. 4, line 56, "[4,3-d]-[1,4]" should read --[4,3-d][1,4]--.

Col. 4, line 60, "[4,3-d]triazepin" should read --[4,3-d][1,4]thiazepin--.

Col. 5, line 58, delete the space between lines.

Col. 7, line 36, "pin3(2H)-ones" should read --pin-3(2H)-ones-

Signed and Sealed this

Third Day of May 1977

[SEAL]

Attest:

RUTH C. MASON
Attesting Officer

C. MARSHALL DANN
Commissioner of Patents and Trademarks